United States Patent [19]
Pero et al.

[11] Patent Number: 6,028,111
[45] Date of Patent: Feb. 22, 2000

[54] COMPOSITIONS AND USE OF BENZAMIDES AND NICOTINAMIDES AS ANTI-INFLAMMATORY AGENTS

[75] Inventors: Ronald W. Pero, Lund, Sweden; David Chaplin, Aston Rowant, United Kingdom

[73] Assignee: OXiGENE, Inc., Boston, Mass.

[21] Appl. No.: 08/807,071

[22] Filed: Feb. 27, 1997

Related U.S. Application Data

[60] Provisional application No. 60/013,072, Mar. 8, 1996.

[51] Int. Cl.⁷ .................................................. A61K 31/165
[52] U.S. Cl. ........................ 514/620; 514/886; 514/887
[58] Field of Search ................................... 514/886, 887, 514/620

[56] References Cited

U.S. PATENT DOCUMENTS

| | | | |
|---|---|---|---|
| 4,146,637 | 3/1979 | Metz et al. | 424/300 |
| 4,263,322 | 4/1981 | van't Riet et al. | |
| 4,394,389 | 7/1983 | van't Riet et al. | |
| 4,448,730 | 5/1984 | van't Riet et al. | |
| 4,623,659 | 11/1986 | van't Riet et al. | |
| 4,942,253 | 7/1990 | van't Riet et al. | |
| 5,183,828 | 2/1993 | van't Riet et al. | |
| 5,350,770 | 9/1994 | Elford et al. | 514/575 |
| 5,366,996 | 11/1994 | Elford et al. | |

FOREIGN PATENT DOCUMENTS

| | | |
|---|---|---|
| 0140958 | 12/1989 | European Pat. Off. |
| 0144396 | 1/1991 | European Pat. Off. |
| 9312782 | 7/1993 | WIPO |

OTHER PUBLICATIONS

Chemical Abstracts AN 1995:886480, Lang et al, "New Antiinflammatory compounds that inhibit TNF production", J. Pharmacol. Exp. Ther. (1995), 275(1), 171–6, Jan. 1995.
Chemical Abstracts AN 1993:670811, Nagar, "A process for the preparation of novel pharmacological active N–substituted benzamide–2–carboxylic acid and their metal complexes", IN 170840 A, May 30, 1992.
Chemical Abstracts AN 1972:14045, "Synthesis and antiinflammatory activity of fluorinated benzamides", Sch. Pharm. Sci. (1971), 60(11), 1723–5, Jan. 1971.
Chemical Abstracts AN 1995:998575, Ali et al., Jan. 1995.
Chemical Abstracts AN 1978:36738, Topart et al., Jan. 1976.
Medline Abstract No. 91244895, Uetrecht et al., Jan. 1991.
Berk et al., *Arch. Dermatol.*, 122:670–74 (1986).
Pozzilli et al., *Diabetes Care*, 17(8):897–900 (1994).
Jonas et al., *Inflamm. Res.* 45:330–34 (1996).
Garcia de Jalon et al., Arzneim.–Forsch./Drug Res. 29(II), Nr. 11:1704–07 (1979).
Nagar et al., *J. Inorg. Biochem.*, 42:9–16 (1991).
Hirohashi et al., Arzneim.–Forsch. Drug Res. 43(I), Nr. 5:569–77 (1993).
Hall et al., *Acta Pharm. Nord.*, 2(6):387–99 (1990).
Dorsey et al., *J. Pharm. Sci.*, 60:1723–25 (1971).
Vernhet et al., *J. Pharmacol. Exp. Ther.* 283:358–65 (1997).
Naik et al., *Ind. J. Exp. Biol.* 17:1353–56 (1979).
Lang et al., *J. Pharmacol. Exp. Ther.* 275:171–76 (1995).
Marak, Jr. et al., *Ophthalmic Res.* 22:111–16 (1990).
Naik et al., *Ind. J. Exp. Biol.*, 16:1169–74 (1978).
Pedrazzoli et al., *Boll. Chim. Farm.*, 115:125–35 (1976).
Hanoeq et al., *J. Pharm. Belg.*, 28(6):649–62 (1973) + translation.
Topart et al., Pharm. Acta Melv. 51(11):314–25 (1976) + translation.
Amiri et al., "Apoptosis in HL–60 cells as aModel . . . " unpub., p. 21 + 6 Figs., submitted to Acta Oncologica (1997).
Baeuerle et al., Cell 87: 13–20 (1996).
Beg et al., Science 274:782–84 (1996).
Bauhayat et al., J. Med. Chem. 28:555–59 (1985).
Harrington et al., Drugs 25: 451–94 (1983).
Horsman, Acta Oncologica 34:571–87 (1995).
King et al., Drugs of the Future 14 (g) : 875–89 (1989).
Moffett et al., J. Med. Chem. 14:963–68 (1971).
Moragues et al., Quim. Ind. (Madrid) 17:104–05 (1971).
Olsson et al., Biochem. Pharmacol. 45:1191–1200 (1993).
Olsson et al.a, Carcinogenesis 16:1029–35 (1995).
Olsson et al., Brit. J. Cancer 74:368–73 (1996).
Pero et al., Biochemie 77:385–93 (1995).
Pero et al., "Multiple Mechanisms of action of the benzamides and nicotinamides . . . ," unpub., p. 21 + 6 sheets of figs., submitted to Cancer Prevent. (1997.
F. Piriou et al., Experimentia 41:1409–10 (1985).
Robert–Piessard et al., Eur. J. Med. Chem. 25:9–19 (1990).
Stanley et al., ed., The Benzamides: Pharmacology, Neurobiology, and Clinical Aspects, Advances in Biochemical Psychopharmacology, vol. 35 (New York: Raven Press, 1982), pp. 1–60, 195–203.
Thompson, Science 267:1456–62 (1995).
VanAntwerp et al., Science 274:787–89 (1996).
Wang et al., Science 274:784–87 (1996).

*Primary Examiner*—Keith D. MacMillan
*Attorney, Agent, or Firm*—Cooper & Dunham LLP

[57] ABSTRACT

The use of benzamide and nicotinamide analogs, in particular N-substituted benzamides and nicotinamides, other than benzamides with N-pyridinyl substitutions, as anti-inflammatory agents.

10 Claims, 5 Drawing Sheets

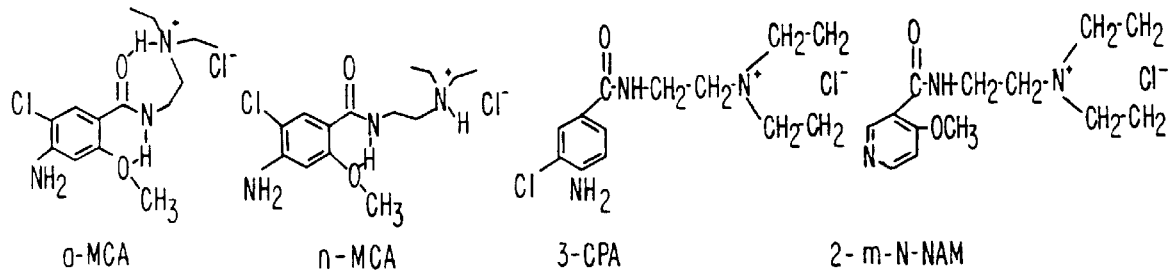
PANEL A: RADIOSENSITIZING N-SUBSTITUTED ANALOGS
o-MCA    n-MCA    3-CPA    2-m-N-NAM
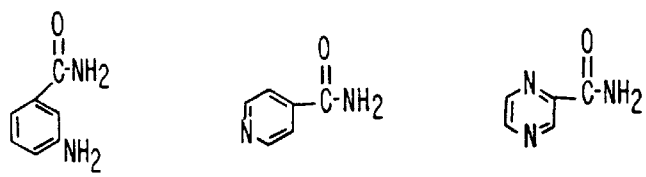
PANEL B: RADIOSENSITIZING NON-N-SUBSTITUTED ANALOGS
3αBAM    NAM    PYRAZIN
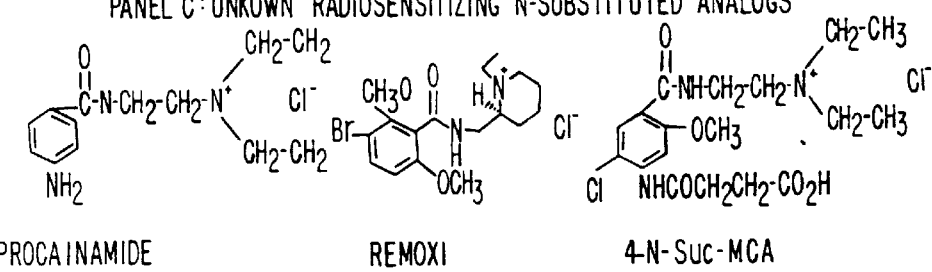
PANEL C: UNKOWN RADIOSENSITIZING N-SUBSTITUTED ANALOGS
PROCAINAMIDE    REMOXI    4-N-Suc-MCA
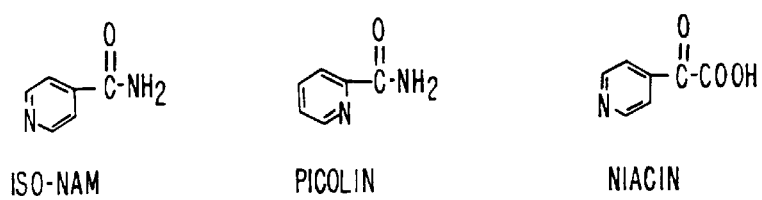
PANEL D: UNKOWN RADIOSENSITIZING NON-N-SUBSTITUTED ANALOGS
ISO-NAM    PICOLIN    NIACIN
FIG. 1

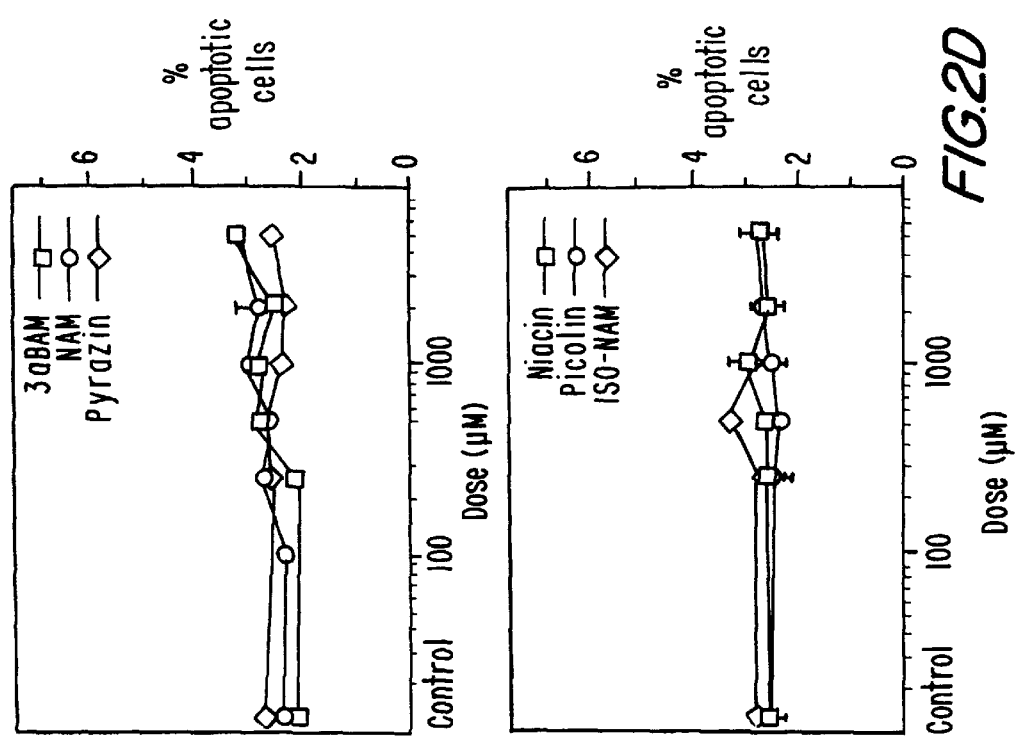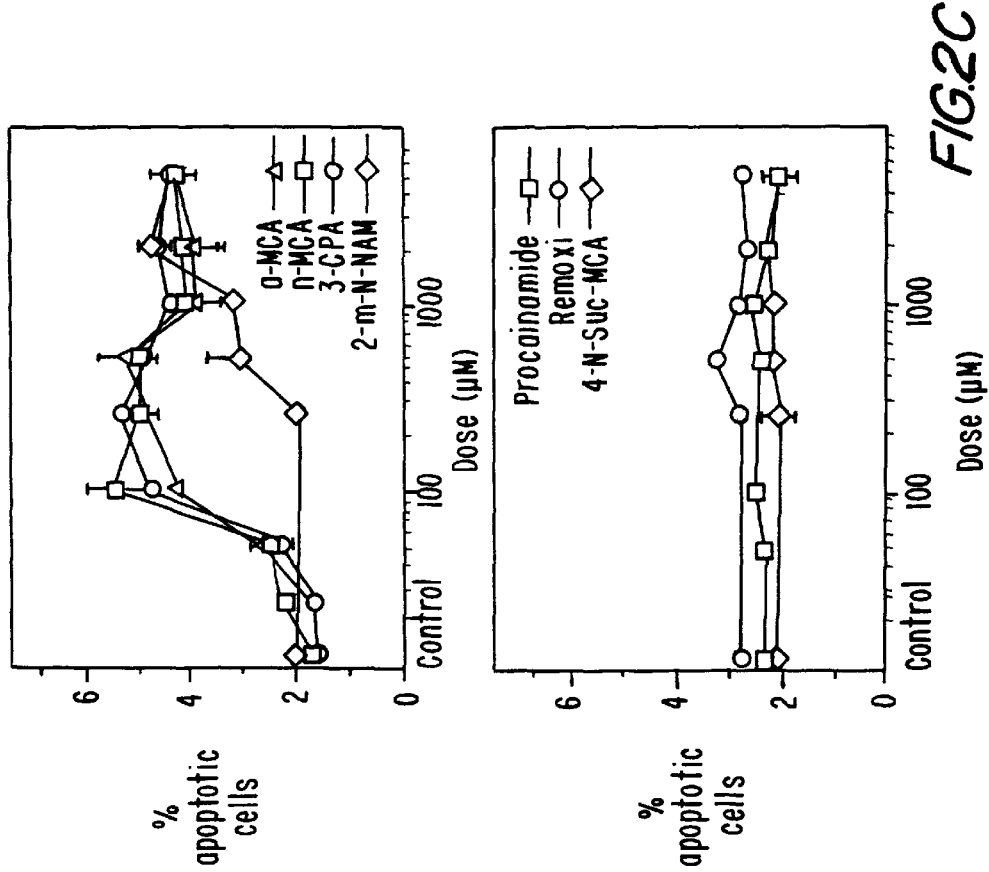

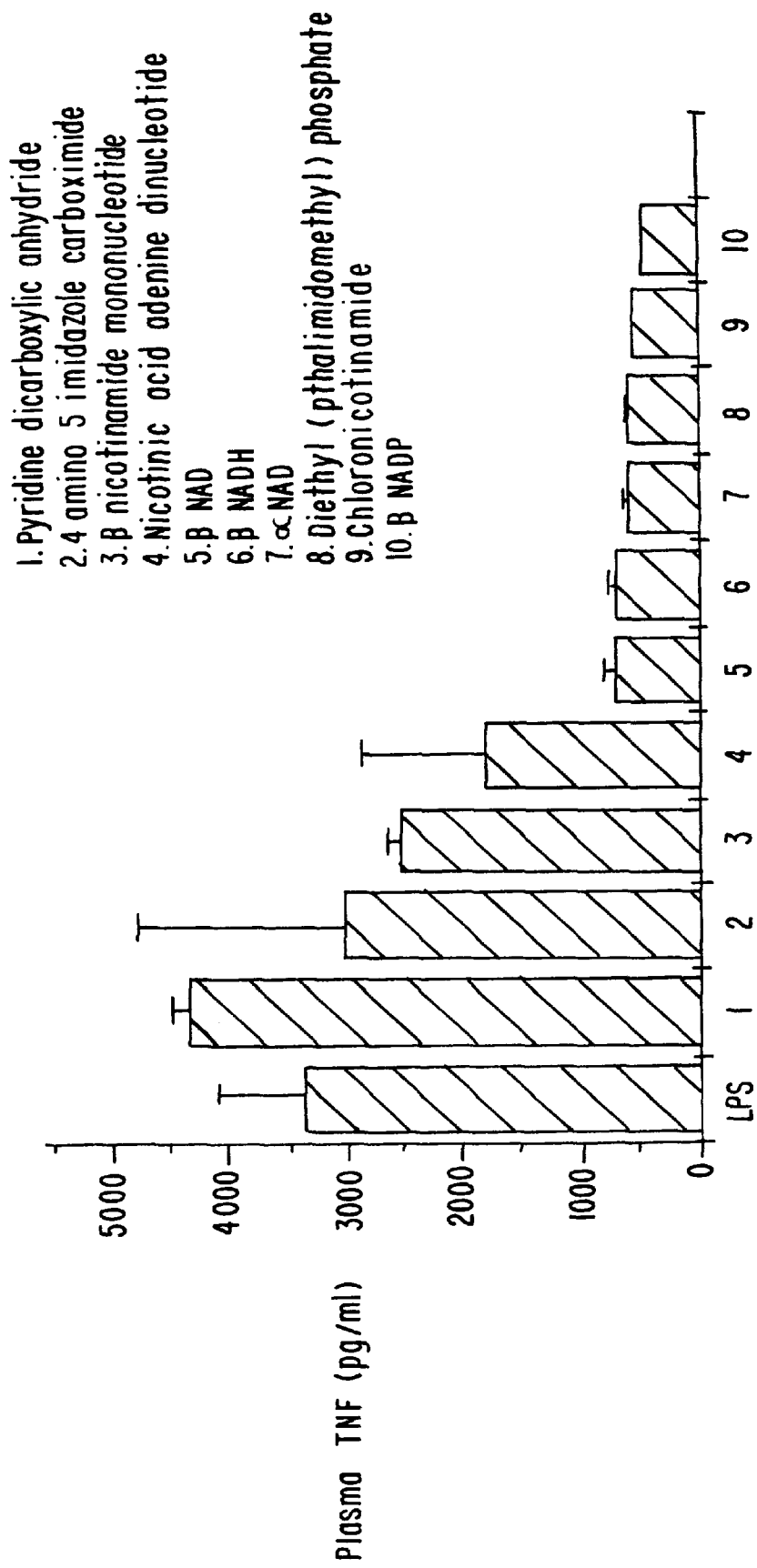

COMPOSITIONS AND USE OF BENZAMIDES AND NICOTINAMIDES AS ANTI-INFLAMMATORY AGENTS

CROSS REFERENCE TO RELATED APPLICATION

This application is a continuation-in-part of U.S. provisional patent application Ser. No. 60/013,072 of Ronald W. Pero et al., filed Mar. 8, 1996, the entire disclosure of which is incorporated herein by this reference.

BACKGROUND OF THE INVENTION

This invention relates to the use of benzamides and nicotinamides, and analogs of this class of compounds such as the N-substituted benzamides and nicotinamides, as anti-inflammatory agents, and to compositions for such use.

The benzamide and nicotinamide analogs are known to possess a wide variety of pharmacological properties including clinical usefulness as anti-arrhythmics, anti-emetics, anti-psychotics, local anaesthetics and radio- and chemosensitizers (Stanley and Rotrosen (eds.), The Benzamides: Pharmacology, Neurobiology and Clinical Aspects, Raven Press, New York, 1982; Horsman, Acta Oncologica 34: 571–587, 1995; Harrington, Drugs 25: 451–494, 1983; Pero et al, Cancer Detection and Prevent., submitted, 1997). These diverse pharmacological properties have been attributed to effects on receptor high affinity binding of signal transducing agents (King and Sanger, Drugs of the Future 14: 875–889, 1989; Olsson et al, Biochem. Pharmacol. 45: 1191–1200, 1993), blood flow (Horsman, Acta Oncologica 34: 571–587, 1995), or inhibited DNA repair and DNA damage accumulation (Pero et al, Biochimie 77: 385–93, 1995; Pero et al, Cancer Detection and Prevent., submitted, 1997; Olsson et al, Carcinogenesis 16: 1029–1035, 1995; Olsson et al, Brit. J. Cancer 74: 368–373, 1996). None of these varied modes of action that so far have been identified with the benzamides or nicotinamides are known to be involved with the pharmacological property of anti-inflammation.

For more than 25 years, it has been indicated in the literature that pyridinyl-N-substituted benzamides have anti-inflammatory properties (Moragues et al, Quim. Ind. (Madrid) 17: 104, 1971; Robert-Piessard et al, Eur. J. Med. Chem. 25: 9–19, 1990). Moreover, it has been reported that these benzamide derivatives also possess anti-ulcerogenic and sedative properties (Moffett et al, J. Med. Chem. 14: 963–968, 1971; Piriou et al, Experientia 41: 1409–1410, 1985; Bouhayat et al, J. Med. Chem. 28: 555–559, 1985). However, in all these studies it was taught that the pyridinyl substitution of the carboxamide of benzamide was selectively anti-inflammatory although other tertiary N-substitutions could be tolerated along with the pyridinyl N-substitution without losing anti-inflammatory, anti-ulcerogenic or sedative activities. As a consequence, so far as the present applicants are aware, no other benzamide, N-substituted or not, has ever been tested for anti-inflammatory properties. The fact that the art has not considered to investigate other benzamide analogs for anti-inflammatory effects, but instead has focused on the N-substituted portion of the molecule, is indicative of the non-obviousness of any inference that the benzamide moiety in itself is useful as an anti-inflammatory agent.

SUMMARY OF THE INVENTION

The present invention, in one broad sense, embraces the discovery that at least some benzamides and nicotinamides can selectively induce apoptosis without having any significant effects on necrosis (U.S. provisional patent application No. 60/013,072 filed Mar. 8, 1996; Pero et al, Cancer Detection and Prevent., submitted, 1997; Amiri et al, Acta Oncologica, submitted, 1997), and that benzamides and nicotinamides (i.e., other than benzamides with N-pyridinyl substitutions) are useful as anti-inflammatory drugs.

By way of partial explanation of the latter discovery, it may be noted that apoptosis is a normal physiological mechanism contributing to the inflammatory development of several disorders including but not limited to cancer, HIV/AIDS, psoriasis, Alzheimer's disease, Hodgkin's disease, Huntington's chorea, ischemic injury, and many other autoimmune and neurodegenerative diseases (Thompson, Science 267: 1456–1462, 1995); hence, the ability of at least some benzamides and nicotinamides to selectively induce apoptosis without having significant effect on necrosis suggests that the benzamides and nicotinamides may be useful as anti-inflammatory drugs.

Also pertinent to an understanding of the foregoing may be the discussions of the molecular biology of inflammation and apoptosis presented in Science 274: 782–789 (Nov. 1, 1996), which set forth that the transcription factor known as nuclear factor kappa B (NF-κB) both inhibits the primary pro-inflammatory cytokine, tumor necrosis factor alpha (TNF-α), and induces apoptotic killing of cells important to the development of new cancer chemotherapeutic strategies. As the benzamides and nicotinamides, particularly the N-substituted analogs, selectively induce apoptosis (U.S. provisional patent application No. 60/013,072 filed Mar. 8, 1996; Pero et al, Cancer Detection and Prevent., submitted, 1997; Amiri et al, Acta Oncologica, submitted, 1997), then NF-κB inhibition being a known regulator of apoptosis may also inhibit the inflammatory response by likewise inhibiting TNF-α production in inflammatory target cells.

More particularly, this invention embraces the discovery that this is the case, i.e., that both the induction of apoptosis and the inhibition of TNF-α are mediated by the benzamides and nicotinamides giving this class of compounds both anti-cancer and anti-inflammatory properties.

The practice of the present invention entails the use of administering to a human or other warm blooded animal: (i) that suffer from an inflammatory disorder such as but not limited to systemic lupus erythromatosis, rheumatoid arthritis, asthma, sepsis, ulcerative colitis, HIV/AIDS, psoriasis, Alzheimer's disease, Hodgkin's disease, Huntington's chorea, ischemic injury, (ii) by an appropriate route such as orally, intravenously, intramuscularly or subcutaneously, (iii) an amount of a benzamide or nicotinamide analog (other than benzamides with N-pyridinyl substitutions) either in a single or repeated dose schedule satisfactory to inhibit TNF-α production in vivo, (iv) that would inhibit the inflammatory response, and (v) that in turn would provide preventive or therapeutic value in controlling health disorders. In another aspect, this invention embraces the discovery that the composition of all benzamide and nicotinamide analogs, other than benzamides that have N-pyridinyl substitutions, are useful in preventing TNF-α production and thus they induce an anti-inflammatory response and have potential preventive or therapeutic value in the clinic. Furthermore, this invention embraces the discovery that benzamides in general and specifically the N-substituted benzamides, other than the pyridinyl-N-substituted benzamides, possess the potent anti-inflammatory properties of inhibiting the production of TNF-α and inducing apoptosis.

Thus, in one sense, the invention contemplates the provision of a method of treating inflammatory disorders comprising administering, to a human or other animal suffering from an inflammatory disorder, an amount of a composition selected from the group consisting of benzamide and nicotinamide analogs and mixtures thereof, other than benzamides with N-pyridinyl substitutions, such amount being effective to inhibit TNF-α production, thereby to inhibit an inflammatory response in the treated human or other animal.

Also in accordance with the invention, in certain advantageous embodiments thereof, the composition comprises, in combination, at least one compound selected from the group consisting of N-substituted benzamides and nicotinamides, other than benzamides with N-pyridinyl substitutions, that can inhibit TNF-α production in the presence of or as a consequence of pro-apoptotic stimuli and at least one compound selected from the group consisting of benzamide and nicotinamide analogs that can inhibit TNF-α in the absence of pro-apoptotic stimuli.

Additionally, the invention contemplates the provision of an anti-inflammatory agent comprising, in combination, at least one compound selected from the group consisting of N-substituted benzamides and nicotinamides, other than benzamides with N-pyridinyl substitutions, that can inhibit TNF-α production in the presence of or as a consequence of pro-apoptotic stimuli and at least one compound selected from the group consisting of benzamide and nicotinamide analogs that can inhibit TNF-α in the absence of pro-apoptotic stimuli.

Specifically, it is found that those N-substituted benzamides and N-substituted nicotinamides that exhibit the property of radiosensitization (e.g., metoclopramide, 3-chloroprocainamide, and 2-methoxy-N-(2-diethyl-aminoethyl)nicotinamide) can inhibit TNF-α production in the presence of or as a consequence of pro-apoptotic stimuli, while benzamides and nicotinamides other than the N-substituted analogs that exhibit the radiosensitizing property can inhibit TNF-α in the absence of pro-apoptotic stimuli.

Further features and advantages of the invention will be apparent from the detailed description hereinbelow set forth, together with the accompanying drawings.

BRIEF DESCRIPTION OF THE DRAWINGS

FIG. 1 is a diagram of the chemical structures of some nicotinamide and benzamide analogs. Abbreviations: a-MCA=acidic metoclopramide; n-MCA=neutral metoclopramide; 3-CPA=3-chloroprocainamide; 2-m-N-NAM=2-methoxy-N-(2-diethyl-aminoethyl)nicotinamide; 3aBAM=3-aminobenzamide; NAM =nicotinamide; Pyrazin= pyrazinamide; Remoxi=remoxipride, niacin, procainamide; 4-N-Suc-MCA=4-N-succinyl-amino metoclopramide; Picolin=picolinamide; and ISO-NAM=isonicotinamide.

FIG. 2 is a graph of the dose response of HL-60 cells exposed in vitro to nicotinamide and benzamide analogs for 6 hours with the cytotoxicity then evaluated using morphological criteria for induction of apoptosis. The number of apoptotic cells is expressed as % of total cells in the cultures. Data points represent mean±SEM of 3 to 5 experiments. The only statistically significant dose dependent effects were determined by linear regression analysis and were: a-MCA, $r=0.779$, $n=28$, $p<0.001$; n-MCA, $r=0.682$, $n=38$, $p<0.001$; 3-CPA, $r=0.753$, $n=38$, $p<0.001$; 2-m-N-NAM, $r=0.531$, $n=14$, $p<0.08$. Drug abbreviations are the same as in FIG. 1.

FIG. 5 is a graph of the inhibition of mouse TNF-α production in plasma induced from a standardized i.p. injection of 1 mg/ml lipopolysaccharide (LPS) administered 2 hours before i.p. injections of 50 mg/kg doses of the indicated nicotinamide analogs. Each bar represents the data from 3 mice.

DETAILED DESCRIPTION OF THE INVENTION

Figure 3A:
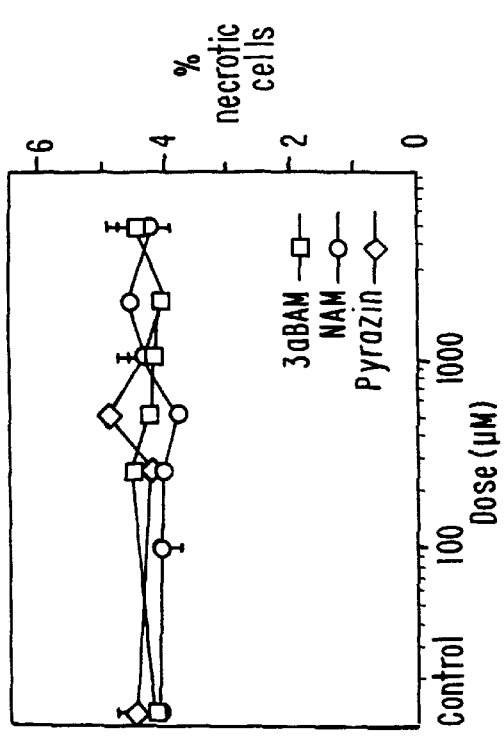
FIG. 3 is a graph of the dose response of HL-60 cells exposed in vitro to nicotinamide and benzamide analogs for 6 hours with the cytotoxicity then evaluated using morphological criteria by induction of necrosis (trypan blue exclusion). Necrotic cells are expressed as % of total cells that did not exclude the dye and data points represents mean±SEM. No statistically significant dose dependent effects were determined for any of the drugs tested. Drug abbreviations are the same as in FIG. 1.
Figure 3B:
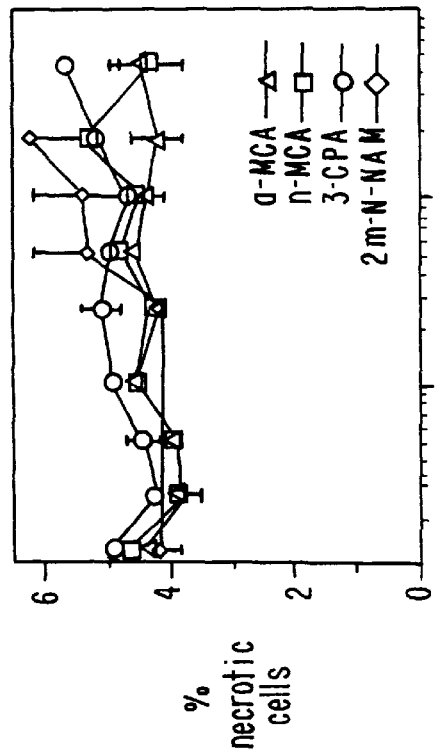
Figure 3C:
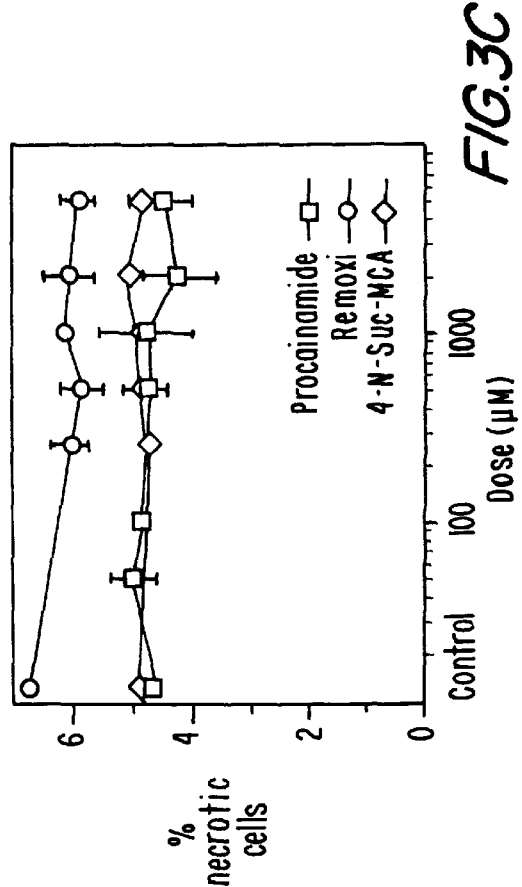
Figure 3D:
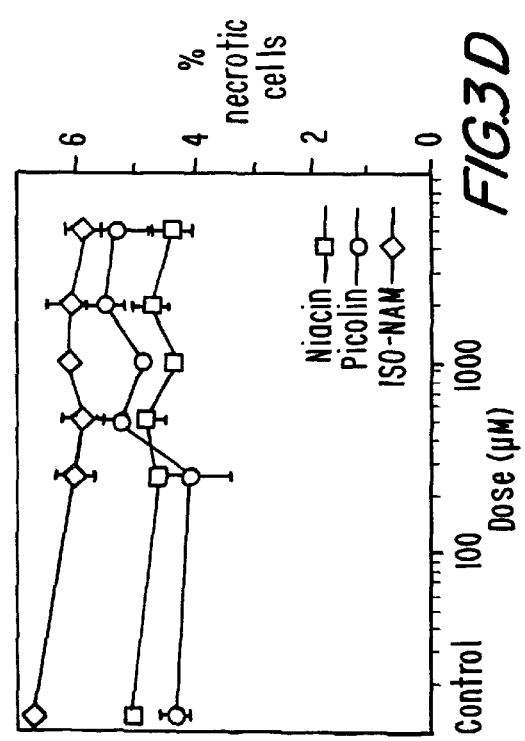

As used herein, the terms "nicotinamide analogs" and "benzamide analogs" include both N-substituted and non-N-substituted nicotinamides and benzamides, and acid addition salts thereof. The term "N-substituted benzamides and N-substituted nicotinamides that exhibit the property of radiosensitization" refers to those compounds, of the designated class, that enhance cytotoxicity when administered in conjunction with radiation as described in the aforementioned U.S. provisional patent application No. 60/013,072 filed Mar. 8, 1996.

The method of the invention as described herein comprises administering, to a human or other warm-blooded animal suffering from an inflammatory disorder, an amount of material selected from the group consisting of nicotinamide analogs and benzamide analogs and mixtures thereof, other than benzamides with N-pyridinyl substitutions, effective to inhibit TNF-α production, thereby to inhibit an inflammatory response in the treated human or other animal. Suitable dosages and selection of particular nicotinamide and/or benzamide analogs will be apparent from the detailed discussion and data set forth in the examples given below.

The methods, experimental design, data and interpretation of the results supporting the claims to this invention are presented in the following Examples 1 and 2. They utilize effects on apoptosis and TNF-α as components of the inflammatory process to show that the benzamides and nicotinamides possess anti-inflammatory properties.

EXAMPLE 1

Chemical structures and data for this Example are set forth in FIGS. 1, 2 and 3.

The design of this experiment was to investigate the relationship between the diversity of the chemical structures of the benzamides and nicotinamides compared to their abilities to induce apoptosis. Apoptosis is an important indirect indicator of inflammation because it is regulated at the molecular level in cells by the same controlling element (i.e., inhibition of transcription factor NF-κB) as the pro-inflammatory cytokine, TNF-α, and because the killing of inflammatory cells by apoptosis is an attractive hypothesis to explain the action of anti-inflammatory drugs that can simultaneously both inhibit TNF-α and induce apoptosis (Beg and Baltimore, Science 274: 782–784, 1996; Wang et al, Science 274: 784–787, 1996; Van Antwerp et al, Science 274: 787–789, 1996).

The in vitro cytotoxicity induced by apoptosis and necrosis were estimated in human promyeloidic leukemic HL-60 cells routinely cultured at a density of $0.5 \times 10^6$ cells.ml$^{-1}$ up to 2 days in 10% calf serum supplemented RPMI medium in a 5% $CO_2$ atmosphere at 37° C. before they were used in cytotoxicity assays. The cells were harvested by centrifugation and resuspended in fresh medium at a concentration of $1 \times 10^6$ cells.ml$^{-1}$ in 15 ml sterile Falcon test tubes for bioassay purposes. Next the cells were exposed to 0–5,000 μM doses of the benzamide and nicotinamide analogs listed in FIG. 1 for 6 hours at 37° C. The cytotoxicity was evaluated as apoptosis and necrosis, where the % apoptotic cells compared to total cells were analyzed and scored by morphological criteria using phase contrast microscopy. The % necrotic cells compared to total cells were determined by trypan blue staining.

The ability of 12 structurally diverse benzamide and nicotinamide analogs to induce apoptosis and necrosis have been evaluated up to doses of 5,000 μM (FIGS. 2 and 3). This example shows that known radiosensitizing N-substituted benzamides and nicotinamides gave a dose dependent activation of apoptosis whereas the N-substituted benzamides not known to possess radiosensitizing properties as well as all the non-N-substituted benzamides and nicotinamides did not induce apoptosis. These effects were paralleled by the lack of any cytotoxicity induced by necrosis as judged by trypan blue exclusion criteria, which in turn has indicated a selective effect on these drugs on the apoptotic pathway. Moreover, these data demonstrate the following important points regarding this invention: (1) The fact that some N-substituted benzamides can elicit pro-apoptotic signals and as such via the common regulatory component, NF-κB, they could simultaneously inhibit TNF-α and could cause cytotoxic killing of inflammatory cells by apoptosis resulting in an anti-inflammatory response, and (2) The remaining N-substituted and the non-N-substituted benzamide and nicotinamide analogs could not elicit apoptosis, and because NF-κB is composed of several complexed regulatory components (Baeuerle et al, Cell 87: 13–20, 1996) it was possible that some may be modulated that inhibit TNF-α without simultaneously eliciting apoptosis. These data, together with that presented in Example 2, clearly establish that the benzamide and nicotinamide analogs may be divided into two mechanistic classes as anti-inflammatory agents; namely, (i) The N-substituted benzamides and nicotinamides that can inhibit TNF-α in the presence of or as a consequence of pro-apoptotic stimuli and (ii) Those benzamides and nicotinamide analogs that can inhibit TNF-α in the absence of pro-apoptotic stimuli. This is an important distinction because many apoptotic signaling agents (e.g. radiation, daunorubicin, and tumor necrosis factor) activate NF-κB which protects against further apoptotic cell killing (Wang et al, Science 274: 784–787, 1996). An important discovery embraced by the present invention is that at least the N-substituted benzamides and N-substituted nicotinamides can both induce apoptosis and inhibit TNF-α (Examples 1 and 2) which is only consistent with an inhibitory effect on NF-κB.

EXAMPLE 2

Figure 4:
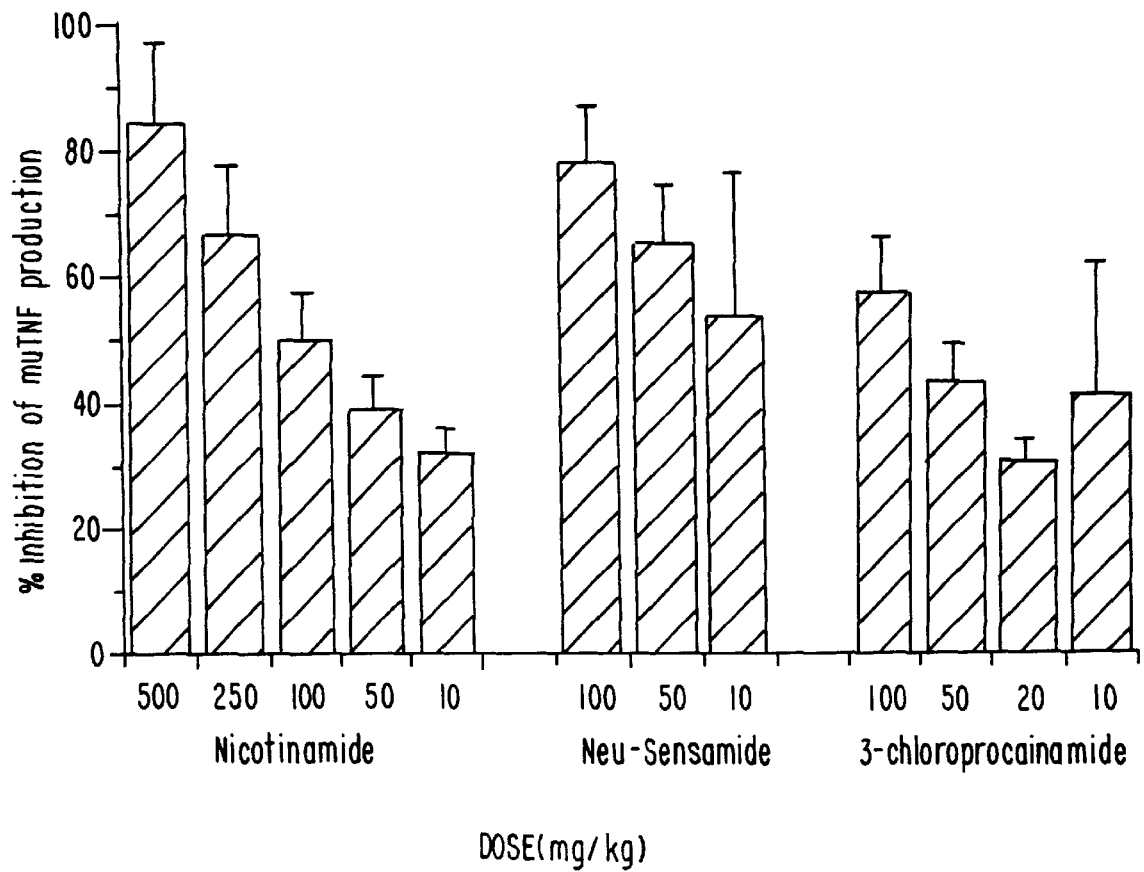
FIG. 4 is a graph of the dose response inhibition of mouse TNF-α production in plasma induced from a standardized i.p. injection of 1 mg/ml lipopolysacharride (LPS) administered 2 hours before i.p. injections of 10–500 mg/kg of nicotinamide, "Neu-Sensamide" (i.e., neutral metoclopramide) and 3-chloroprocainamide. Each bar represents the results from 9 mice.

The data for this Example are set forth in FIGS. 4 and 5.

The ability of benzamide and nicotinamide analogs to inhibit the production of TNF-α in vivo was evaluated using 16–24 week old male CBA mice weighing 35–40 grams. The test drugs were administered by intraperitoneal (i.p.) injection at the doses indicated in FIGS. 4 and 5 in volumes of 0.1 ml saline per 10 grams body weight, which also contained the test drug at the final desired doses, 15 minutes before a 1 mg/kg i.p. injection of lipopolysaccharide (LPS, *E. coli* serotype 0111:B4). Blood samples were collected 2 hours later into a heparinized syringe, centrifuged at 1614×g for 5 minutes, the plasma removed from the supernatant fraction, and then stored at −20° C. until analysis of TNF-α.

The production of TNF-α in plasma following a standardized inductive treatment in vivo by LPS was estimated using a murine TNF-α solid-phase ELISA and a multiple antibody sandwich principle. 96-well flat-bottomed, high binding microtiter plates were pre-coated with 10 μg/ml (i.e. 50 μl per well) Hamster anti-mouse TNF-α (Genzyme 1221) in 0.1M $NaHCO_3$ (pH 8.2) at 4° C. which is used to capture any TNF-α present in the plasma samples or standards. The plates were washed twice with 0.01 Tween 20 in phosphate buffered saline, and then blocked for 30 minutes at 37° C. using 10% fetal calf serum (FCS) in phosphate buffered saline (PBS). Next the blocking buffer was removed by washing two times with the Tween 20 buffer. 100 μl per well aliquots of a standard murine TNF-α (i.e., 0–2,000 picograms/ml, Genzyme) and plasma samples (diluted with 10% FCS in PBS) were left overnight at 4° C. and then washed 4 times with the Tween buffer. 50 μl polyclonal rabbit anti-mouse TNF-α (1:500 dilution, Genzyme IP400) in 10% FCS in PBS which binds to the captured TNF-α was incubated for 2 hours at room temperature and then washed 4 times with the Tween 20 buffer. 100 μl per microtiter-well of goat anti-rabbit IgG peroxidase-conjugated polyclonal antibody (1:200, Sigma A6154) prepared in 10% FCS in PBS was added for 1 hour at room temperature and then washed 4 times with the Tween 20 buffer. 100 μl of a substrate solution per microtiter-well containing 0.4 mg/ml o-paraphenyldiamine (Sigma P7288) in 0.05 M citrate-phosphate buffer, pH 5.0 and hydrogen peroxide (20 μl of 30% hydrogen peroxide per 50 ml of paraphenyldiamine solution) was added to initiate a peroxidase catalyzed color change that was subsequently stopped by addition of 25 μl of 3 M $H_2SO_4$. The A 492 nm was proportional to the concentration of TNF-α and the unknown levels in the plasma samples were determined by comparison to a standard curve of known concentrations of plasma- spiked, purified TNF-α samples.

A total of 13 benzamide and nicotinamide analogs were evaluated for their abilities to inhibit in vivo the LPS-stimulated production of TNF-α in mouse plasma (FIGS. 4 and 5). There was a measurable inhibition of TNF-α production for 10 of the 13 compounds tested at the indicated physiological relevant dose levels. These data confirm that the apoptotic-inducing N-substituted benzamides also inhibit TNF-α giving them pharmacological anti-inflammatory properties as well as properties to control tumor growth (Wang et al, Science 274: 784–787, 1996). In addition, they show that non-N substituted analogs specifically of nicotinamides, and in general of benzamides by reference to disclosures already made therein (e.g., non-N-substituted benzamides and nicotinamides are indistinguishable with regard to their known biochemical and pharmacological properties; Pero et al, Cancer Detection and Prevent., submitted, 1997), can likewise inhibit TNF-α and thereby possess anti-inflammatory properties. In conclusion, these data disclose that most but not all benzamide and nicotinamide analogs can inhibit TNF-α, and as such, are useful candidate drugs for clinical development as anti-inflammatory drugs.

Synthesis of 3-chloroprocainamide

Following is a description of the synthesis of 3-chloroprocainamide as set forth in the aforementioned U.S. provisional patent application No. 60/013,072.

The compound 3-chloroprocainamide (N-(2-diethylamino-ethyl)- 4-amino-3-chlorobenzamide), and its hydrochloride, can be synthesized by the following procedures:

Novel synthesis of 3-chloro-procainamide hydrochloride [N-(2-diethylamino-ethyl)-4-amino-3-chlorobenzamide hydrochloride] (1a)

3-Chloroprocainamide Hydrochloride (1a)

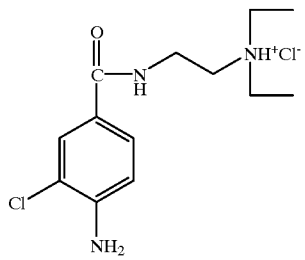

(1a)

Ethyl 4-amino-3-chlorobenzoate (2)

Ethyl p-aminobenzoate, 49.50 g (0.30 moles) was dissolved in 500 ml of acetonitrile ($CH_3CH$) and heated to reflux. When the mixture became homogeneous, 42.0 g (0.315 moles) of N-chlorosuccinimide was added in several portions over one hour and the mixture was stirred at reflux overnight. By TLC (Hexane: EtOAc, 3:1), the mixture contained no starting material but only the desired product (Rf=0.55) and a minor impurity, which was probably dichlorinated material (Rf=0.65). The mixture was concentrated on a rotary evaporator and the residue was redissolved in 250 mL of dichloromethane ($CH_2Cl_2$) and washed twice with 100 mL of 5% sodium hydroxide (NaOH). The organic layer was dried over anhydrous potassium carbonate ($K_2CO_3$) and concentrated on a rotary evaporator to yield 62.0 g of a reddish brown solid. The solid was recrystallized from 1.25 L of boiling hexane to give 52 g of a brown solid. The solid was recrystallized twice more from 1 L of boiling hexane to give 45.5 g (76%) of tan solid ethyl 4-amino-3-chlorobenzoate (2), mp 82–83° C. and homogeneous by TLC. Additional material, 9.6 g (16%) of like quality, was obtained by repeated recrystallization from hexane. The total yield of pure ethyl 4-amino-3-chlorobenzoate (2) was 92%. 1H NMR ($CDCl_3$) d 7.97– 7.96 (t, 1H, J=0.7 Hz, ArH), 7.80–7.75 (dt, 1H, J=0.7 Hz, ArH), 6.77–6.73 (dd, 1H, J=0.5 Hz, ArH), 4.40–4.29 (q, 2H, J=2.8 Hz, $OCH_2$), 1.41–1.34 (t, J=2.8 Hz, 2H, $OCH_2CH_3$). IR (KBr) $cm^{-1}$, 3500, 3370 ($NH_2$, m), 1695, (C=O, s) 1630. MS (EI) m/e 199 (M+), 201 (M+2), Anal. Calc'd for $C_9H_{10}NO_2Cl$: C, 54.15; H, 5.05: N, 7.02. Fd. C, 54.14; H, 5.17, N, 6.93. The formula is:

Ethyl 4-Amino-3-chlorobenzoate (2)

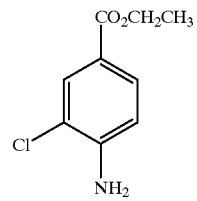

(2)

4-Amino-3-chlorobenzoic acid (3)

The benzoate ester (2), 45.5 g (0.23 moles), was dissolved in 250 mL of hot MeOH and then 230 mL of 3N NaOH (3 equivalents, 0.69 moles) was added. The mixture was stirred at reflux for 5 hours. The solution was concentrated on a rotary evaporator at 80° C. to remove the MeOH and then the mixture was acidified to pH 2 with 3N HCl. The precipitated solids were filtered on a sintered glass funnel and washed with water. The product was homogeneous by TLC (Hexane: EtOAc, 4:1, Rf=0.1) and therefore was not further purified. The white solid was dried at 70° C. in a vacuum oven to give 38.1 (97%) of 4-amino-3 chlorobenzoic acid (3), mp 225–226° C. 1H NMR (DMSO $d_6$) d 7.70 (d, 1H, J=0.9 Hz, ArH), 7.61–7.56 (dd, 1H, J=0.7 Hz, ArH), 6.78 (d, 1H, J=3.4 Hz, ArH), 6.15 (bs, 2H, $NH_2$). IR (KBr) $cm^{-1}$, 3515, 3410 ($NH_2$, m), 1675, (C=O, s) 1640. MS(EI) m/e 171 (M+), 173 (M+2). Anal.

Calc'd for $C_7H_6NO_2Cl$: C, 49.00; H, 3.62; N, 8.16. Fd. C, 49.22; H, 3.71, N, 7.9. The formula is:

4-Amino-3-chlorobenzoic Acid (3)

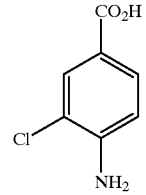

(3)

3-chloro-procainamide, free base, [N-(2-diethylamino-ethyl)-4-amino-3-chlorobenzamide, free base] (1b)

The acid (2), 10 g (0.058 moles) was dissolved in 800 mL of anhydrous THF. Carbonyl diimidazole, 11.1 g (0.067 moles), was added in one portion and the mixture was warmed to 35° C. $CO_2$ began to slowly evolve and then increased rapidly. After one hour, all evolution of gas ceased and the mixture was warmed to 45° C. for fifteen minutes to insure that all of the acid had reacted. N,N'-diethylenediamine, 7.5 g (0.65 moles) was added dropwise over five minutes and then the reaction mixture was warmed to 55° C. After 30 minutes, a TLC of the mixture ($CH_2Cl_2$:MeOH, 3:1) showed that the reaction was complete, producing the desired product (Rf 0.4) along with a minor nonpolar impurity (Rf 0.8) and polar impurities (Rf 0.1). The TCL did not change after stirring overnight at 55° C. The solvent was removed on a rotary evaporator at 50° C. and then 100 mL of water was added to destroy any unreacted carbonyl diimidazole, producing a biphasic mixture. The free base was extracted into $CH_2Cl_2$ (3×100 mL), and dried over anhydrous $K_2CO_3$, and evaporated to give 20 g (>100%) of a brown oil. Attempts to prepare a crystalline salt (sulfate, succinate, tosylate, and adipate) failed. Simple chromatography on 25 g of silica, eluting with hexane :

EtOAc (2:1) gave 14.3 g (91%) of 1b as clear tan oil, homogeneous by TLC. The structure of the free base (1b) is shown in FIG. 5. 1H NMR (CDCL$_3$) d 7.75 (d, J=0.8 Hz, 1H, ArH), 7.52–7.48 (dd, J=0.8 Hz, 1H, ArH), 6.84 (bs, 1H, NH), 6.77–6.74 (d, J=2.8 Hz, 1H, ArH), 3.49–3.43 (q, 2H, J=1.8 Hz, CH$_2$NHCO), 2.66–2.54 (m, 6H, (CH$_2$)$_3$N, 1.07–1.02 (t, J=2.4 Hz, 6H, N(CH$_2$CH$_3$)$_2$). IR (KBr) cm$^{-1}$, 3475, 3320 (NH$_2$, m), 1620, 1600 (C=O, s). MS (El) m/e 269 (M+), 271 (M+2), 240 (M=—Et), 197 (M+-NEt$_2$), 154 (M+—NCH$_2$CH$_2$NEt$_2$), 86 (base peak, M+—CH$_2$NEt$_2$) Anal. Calc'd for C$_{13}$H$_{20}$N$_3$OCl: C, 57.88; H, 7.47; N, 15.58. Fd. C, 58.05; H, 7.56; N, 15.30. The formula is:

3-Chloroprocainamide, free base (1b)

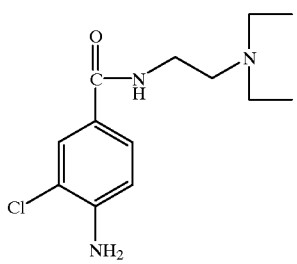

(1b)

N-(2-diethylamino-ethyl)-4-amino-3-chlorobenzamide hydrochloride (1a)

The free base (1b) 22.1 g (0.082 moles) was placed in a flask and acidified to pH 2 with 85 mL of 1N HCl. The homogenous light yellow solution was divided up equally in five pre-weighed 100 mL lyophilization vials and frozen to −80° C. and lyophilized at high vacuum for one week in a Virtis Freeze-Dryer. Each vial was confirmed to contain 5.0 g (+0.1 g) of amorphous lyophilized material that was determined to be deliquescent. The yield of the hydrochloride (1a) was 100%. 1H NMR (D$_2$O) d 7.87 (s, 1H, ArH), 7.66 (d, J=2.8 Hz, 1H, ArH), 7.47 (s, 1H, NH), 7.29 (d, J=2.8 Hz, 1H, ArH), 3.74–3.78 (t, J=2.0 Hz, 2H, CH$_2$NHCO), 3.42–3.25 (m, 6H, (CH$_2$)$_3$N), 1.33–1.28 (t, J=2.4 Hz, 6H, N(CH$_2$CH$_3$)$_2$) IR (KBr) cm$^{-1}$, 3230 (NH$_2$, m), 1630, (C=O, s). Anal.Calc'd for C$_{13}$H$_{20}$N$_3$OCl.HCl.2H$_2$O) C, 45.95; H, 6.47; N, 12.26. Fd. C, 45.62; H, 6.90; N, 12.28.

The present invention in a further aspect contemplates the provision of a method of treating emesis comprising administering, to a human or other animal, an amount of 3-chloroprocainamide effective to prevent or reduce emesis. This method is illustrated by the following additional Example:

EXAMPLE 3

The antiemetic properties of 3-chloroprocainamide were evaluated in beagle dogs where vomiting was induced by cisplatin treatment.

Dogs were randomly assigned to receive either 0, 10, 20 or 40 mg/kg of 3-chloroprocainamide intramuscularly (i.m.) (n=5/dose group). Dogs were instrumented with jugular catheters, food and water were removed from their cages/runs and 0.9% NaCl diuresis (10 ml/kg/hr) initiated by 9:00 a.m. 3-chloroprocainamide or sham injection (0.9% NaCl) were administered (IM) at the beginning of the first and last hour of saline diuresis (hour 0 and 7). The volume of the sham injection was randomized to the volume equivalent to that when 3-chloroprocainamide was administered (0.1, 0.2 or 0.4 mL/kg). One hour after the test compound or sham injection, cisplatin was administered (70 mg/m$^2$ IV) in 0.9% NaCl as a one hour infusion. All dogs continued to receive 0.9% NaCl for six hours after cisplatin was administered.

Emesis onset was determined as the time from the end of cisplatin infusion to first vomiting episode. Acute (early) emesis was defined as vomiting observed during the eight hour infusion/observation period. Dogs and their cage/run floor were examined every 15–20 minutes and they were monitored during infusion for evidence of hypersalivation, vomiting or retching.

The grading scale for early nausea and vomiting was: 0=no evidence of hypersalivation, vomiting or retching; 1=hypersalivation, no vomiting or retching; 2=hypersalivation and 1–2 vomiting episodes (cluster of vomits±retching separated by ≧5 minutes) and the total number of vomits in all episodes was <5 and all episodes were ≦10 minutes; 3=1–2 episodes of vomiting/retching and the total number of vomits was ≧5 but <10 and any episode was >10 minutes duration; 4=vomiting episodes ≧3, and the total number of vomits was ≧5 but <10; 5=vomiting episodes >5 or total vomits ≧10.

The data in Table 1 were analyzed by logistical regression analysis to determine dose related effects.

Acute (early) emesis was observed in all control dogs and in dogs receiving either 10 or 20 mg/kg of 3-chloroprocainamide. Emesis was observed in 2/5 dogs receiving 40 mg/kg of 3-chloroprocainamide. Emesis frequency, latency, duration and severity are listed in Table 1. Emesis frequency and severity decreased as a function of dose (p<0.001; Table 1). Emesis latency increased as a function of dose (p<0.002; Table 1). However, emesis duration was not dose-dependent. These findings conclusively demonstrate the antiemetic effect of 3-chloroprocainamide.

TABLE 1

Acute (early) emesis frequency, latency, duration, and grade in dogs receiving 70 mg/m$^2$ cisplatin and either 0, 10, 20 or 40 mg/kg cf 3-chloroprocainamide.

| 3-Chloroprocainamide | | Emesis Frequency | Emesis Onset(min) | Emesis Grade |
|---|---|---|---|---|
| | 0 | 8 | 115 | 4 |
| | 0 | 11 | 99 | 5 |
| | 0 | 16 | 99 | 5 |
| | 0 | 24 | 62 | 5 |
| | 0 | 29 | 93 | 5 |
| Avg. | — | 17.6 | 93.6 | 4.8 |
| | 10 | 5 | 87 | 4 |
| | 10 | 2 | 2 | |
| | 10 | 7 | 98 | 5 |
| | 10 | 8 | 97 | 5 |
| | 10 | 6 | 120 | 4 |
| Avg. | — | 5.6 | 100.5 | 4.0 |
| | 20 | 5 | 108 | 4 |
| | 20 | 0 | 0 | |
| | 20 | 5 | 126 | 4 |
| | 20 | 3 | 106 | 2 |
| | 20 | 6 | 100 | 4 |
| Avg. | — | 3.8 | 110 | 2.8 |
| | 40 | 0 | 0 | |
| | 40 | 0 | 1 | |
| | 40 | 6 | 4 | |
| | 40 | 1 | 326 | 2 |
| | 40 | 0 | 0 | |
| Avg. | — | 1.4 | 326 | 1.4 |

It is to be understood that the invention is not limited to the features and embodiments hereinabove specifically set forth, but may be carried out in other ways without departure from its spirit.

What is claimed is:

1. A method of treating inflammatory disorders comprising administering, to a human or other animal suffering from an inflammatory disorder, an amount of a composition selected from the group consisting of N-substituted benzamides capable of forming acid addition salts and capable of inhibiting TNF-α and/or selectively inducing apoptosis and N-substituted nicotinamides capable of forming acid addition salts and capable of inhibiting TNF-α and/or selectively inducing apoptosis, and acid addition salts thereof and mixtures thereof, other than metoclopramide and benzamides with N-pyridinyl substitutions, said amount being effective to inhibit TNF-α production, thereby to inhibit an inflammatory response in said human or other animal.

2. A method according to claim 1, wherein said composition is selected from the group consisting of N-substituted benzamides and N-substituted nicotinamides that exhibit the property of radiosensitization and are capable of forming acid addition salts and capable of inhibiting TNF-α and/or selectively inducing apoptosis, acid addition salts thereof, and mixtures thereof, other than metoclopramide.

3. A method according to claim 2, wherein said composition is selected from the group consisting of 3-chloroprocainamide, 2-methoxy-N-(2-diethylaminoethyl)nicotinamide, acid addition salts thereof, and mixtures thereof.

4. A method of treating inflammatory disorders comprising administering, to a human or other animal suffering from an inflammatory disorder, an amount of a composition selected from the group consisting of 3-chloroprocainamide and acid addition salts thereof, and mixtures thereof, said amount being effective to inhibit TNF-α production, thereby to inhibit an inflammatory response in said human or other animal.

5. A method according to claim 3, wherein said composition is selected from the group consisting of 2-methoxy-N-(2-diethylaminoethyl)nicotinamide and acid addition salts thereof, and mixtures thereof.

6. A method of treating inflammatory disorders comprising administering, to a human or other animal suffering from an inflammatory disorder, an amount of a composition comprising, in combination, at least one compound (i) selected from the group consisting of N-substituted benzamides and N-substituted nicotinamides, other than metoclopramide and benzamides with N-pyridinyl substitutions, that can inhibit TNF-α production in the presence of or as a consequence of pro-apoptotic stimuli and at least one compound (ii) selected from the group consisting of benzamide and nicotinamide analogs that can inhibit TNF-α in the absence of pro-apoptotic stimuli, said amount being effective to inhibit TNF-α production, thereby to inhibit an inflammatory response in said human or other animal.

7. A method according to claim 6, wherein said at least one compound (i) is selected from the group consisting of N-substituted benzamides and N-substituted nicotinamides that exhibit the property of radiosensitization, acid addition salts thereof, and mixtures thereof.

8. A method according to claim 7, wherein said at least one compound (i) is selected from the group consisting of 3-chloroprocainamide, and 2-methoxy-N-(2-diethylaminoethyl)nicotinamide, acid addition salts thereof, and mixtures thereof.

9. A method of treating inflammatory disorders comprising administering, to a human or other animal suffering from an inflammatory disorder, an amount of a composition selected from the group consisting of non-N-substituted benzamide and nicotinamide analogs capable of inhibiting TNF-α and selectively inducing apoptosis and mixtures thereof, other than metoclopramide said amount being effective to inhibit TNF-α production, thereby to inhibit an inflammatory response in said human or other animal.

10. A method of treating inflammatory disorders comprising administering, to a human or other animal suffering from an inflammatory disorder, an amount of a composition selected from the group consisting of β nicotinamide mononucleotide, nicotinic acid adenine dinucleotide, β NAD, β NADH, α NAD, diethyl (phthalimidomethyl) phosphate, chloronicotinamide, and β NADP, said amount being effective to inhibit TNF-α production, thereby to inhibit an inflammatory response in said human or other animal.

* * * * *